US00PP37646P2

(12) United States Plant Patent
Hansen

(10) Patent No.: US PP37,646 P2
(45) Date of Patent: Aug. 25, 2026

(54) ***HOSTA* PLANT NAMED 'Brontosaurus'**

(50) Latin Name: ***Hosta* hybrid**
Varietal Denomination: Brontosaurus

(71) Applicant: Hans A. Hansen, Zeeland, MI (US)

(72) Inventor: Hans A. Hansen, Zeeland, MI (US)

(73) Assignee: Walters Gardens, Inc, Zeeland, MI (US)

( * ) Notice: Subject to any disclaimer, the term of this patent is extended or adjusted under 35 U.S.C. 154(b) by 0 days.

(21) Appl. No.: 18/831,966

(22) Filed: Dec. 11, 2025

(51) Int. Cl.
*A01H 5/02* (2018.01)
*A01H 6/12* (2018.01)

(52) U.S. Cl.
USPC ..... Plt./353

(58) Field of Classification Search
USPC ..... Plt./263.1, 353
See application file for complete search history.

(56) References Cited

U.S. PATENT DOCUMENTS

PP12,402 P2 * 2/2002 Hansen ..... A01H 5/02 Plt./353
PP36,700 P2 * 5/2025 Hansen ..... Plt./353

* cited by examiner

*Primary Examiner* — Karen M Redden

(57) ABSTRACT

A new and distinct *Hosta* plant named 'Brontosaurus' having large mounds. The foliage is flat, broadly ovate, acute apices, cordate bases with variegation having light yellow margins and dark-green centers and intermediate color separation between the margin and center of variably shades of chartreuse. The broadly campanulate flowers are near white with light purple blush appearing tightly congested on scapes just above the foliage beginning in early July. 'Brontosaurus' is useful in the landscape as a specimen or en masse.

2 Drawing Sheets

Botanical classification: *Hosta* hybrid (Tratt.).
Variety denomination: 'Brontosaurus'.

STATEMENT REGARDING PRIOR DISCLOSURES UNDER 37 CFR 1.77(B)(6)

*Hosta* 'Brontosaurus' was first introduced by the inventor as a non-enabling description in registration of the name in early 2025 with the International Cultivar Registration Authority for the genus *Hosta*. No plants of *Hosta* 'Brontosaurus' have been sold in this country or anywhere in the world, nor has any enabling disclosure of the new plant been made.

BACKGROUND AND ORIGIN OF THE PLANT

The present invention relates to a new and distinct *Hosta* plant, *Hosta* 'Brontosaurus' hereinafter also referred to as the new plant or by the cultivar name 'Brontosaurus'. *Hosta* 'Brontosaurus' was hybridized by the inventor on Jun. 25, 2012, at a wholesale perennial nursery in Zeeland, Michigan, USA. The female parent was the proprietary unreleased hybrid known only as WGI-22A (not patented) and the male parent was 'Empress Wu' U.S. Plant Pat. No. 20,774. The seeds from this cross were planted in early spring of 2013 and a single seedling selection from this cross was eventually selected as the new plant. The new plant was assigned the breeder code 12-156-2 and passed the initial evaluation in the summer of 2015.

'Brontosaurus' has been asexually propagated by division at the same nursery since 2023, and also by careful shoot tip plant tissue culture with the resultant asexually propagated plants having retained all the same traits as the original plant. *Hosta* 'Brontosaurus' has been stable and reproduced true to type plants in successive generations of asexual reproduction.

There are over 7,000 registered and established *Hosta* cultivars with The American *Hosta* Society, which is the International Cultivar Registration Authority for the genus *Hosta*. Several of these have blue-green leaf blades. The most similar *Hosta* cultivars known to the applicant are: 'All that Jazz' (not patented), 'Earth Angel' (not patented), 'Leading Lady' (not patented), 'Terms of Endearment' U.S. Plant Pat. No. 34,806, 'Titanic' (not patented), 'Victory' U.S. Plant Pat. No. 12,402, and 'Wu-La-La' U.S. Plant Pat. No. 31,309.

'All that Jazz' has a smaller habit, the variegated margin is narrower with less pronounced intermediate coloration, and the center is slightly less glaucous. 'Earth Angel' is more arching in habit with a more glaucous adaxial leaf surface, the margin is more sinuate, and the flowers are less flared. 'Leading Lady' has a slightly smaller habit and smaller foliage with a more creamy white and flowers that are pale lavender. 'Terms of Endearment' has a slightly smaller habit and smaller foliage that is more glaucous and more bullate. 'Titanic' has a slightly smaller habit and smaller foliage that has a stiffer and thicker substance with broader yellowish margins and bluish-green center. The flowers more moderate purple. 'Victory' has the leaves are lightly bullate and matte above, and the flowers are light bluish-lavender on taller scapes. 'Wu-La-La' has a slightly smaller habit, slightly glaucous, stiffer and thicker foliage with a darker yellow margin, and the flowers are light lavender.

The female parent is larger and taller with larger foliage that is streaked variegation thinly spread out in sectors throughout the leaves rather than with the yellowish sector all being confined to the middle of the leaves, and the scape is more upright. The male parent larger with solid bluish-green colored foliage, and the scapes are more arching and lower to the ground.

Other *Hosta* cultivars may have individual traits similar to 'Brontosaurus' but the new plant differs from the above listed cultivars and all other *Hostas* known to the applicant, by the combination of the following traits.

1. Leaves are large, broadly ovate, with acute apices and cordate bases;
2. Leaves flat with impressed adaxial veins;
3. Leaf center is lustrous dark-green and margins emerge yellowish-green and mature to a light yellow with intermediate color separation between the margin and center of variably large segments of several shades of chartreuse;
4. Broadly campanulate flowers are near white with a pale purple blush appearing tightly congested just above the foliage on arching scapes beginning in early-July;
5. Light green floral bracts subtend each flower;
6. The habit is a large mound.

BRIEF DESCRIPTION OF THE DRAWING

The photograph of the new plant demonstrates the overall appearance of the new plant, including the unique traits. The colors are as accurate as reasonably possible with color reproductions. Ambient light spectrum, temperature, source and direction may cause the appearance of minor variation in color.

The drawings show an eight-year-old 'Brontosaurus' plant in a trial garden at a nursery in Zeeland, MI with supplement fertilizer and water as needed.

DETAILED BOTANICAL DESCRIPTION

Figure 1:
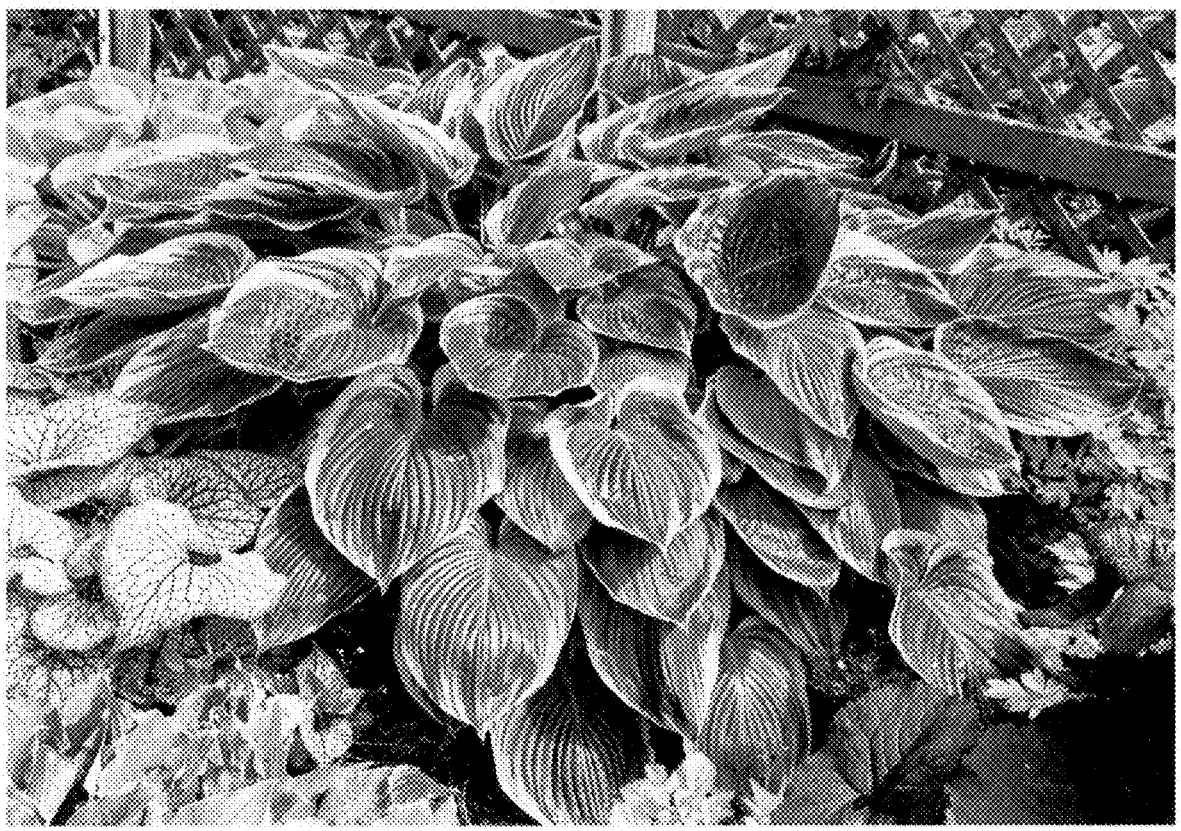
FIG. 1 shows the landscape foliage habit of a new plant in mid-summer.
Figure 2:
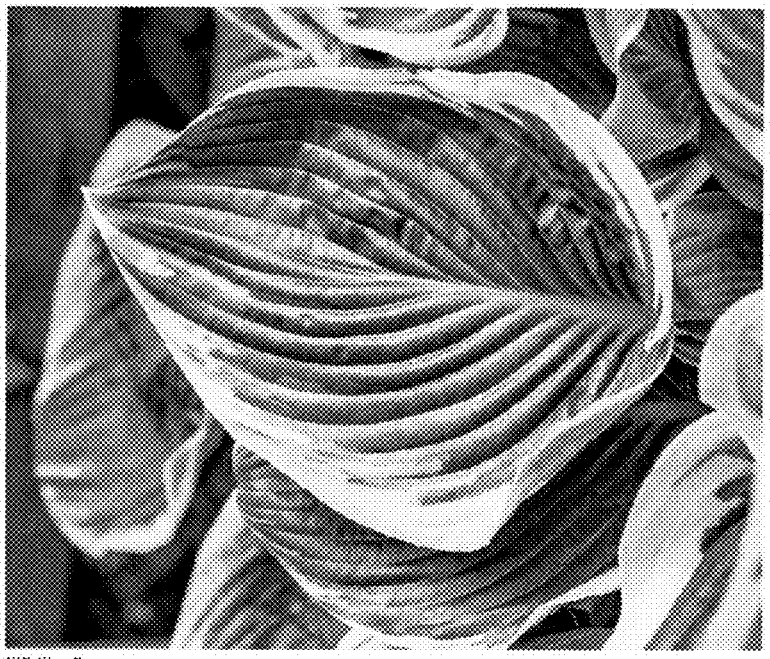
FIG. 2 shows a close-up of a leaf.
Figure 3:
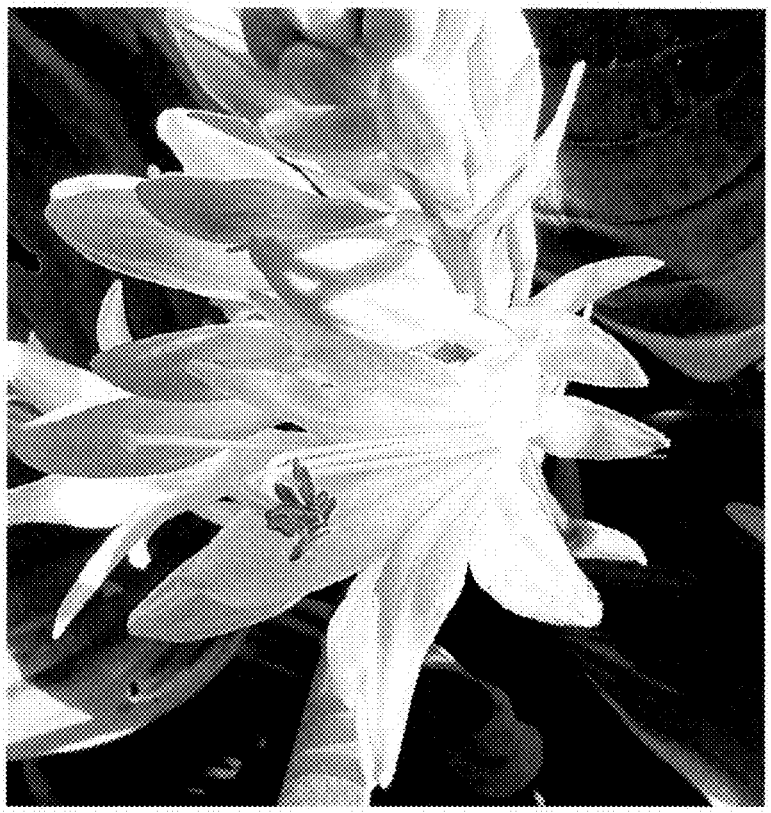
FIG. 3 shows a close-up of the scape with flower, buds, and foliar bracts.

The following descriptions and color references are based on the 2015 edition of The Royal Horticultural Society Colour Chart except where common dictionary terms are used. The new plant, *Hosta* 'Brontosaurus', has not been observed under all possible environments. Those skilled in the art will appreciate that certain characteristics will vary with plants that are more mature or plants that are less mature. The phenotype may vary slightly with different environmental conditions, such as temperature, light, fertility, moisture and maturity levels, but without any change in the genotype. The following observations and size descriptions are of a eight-year-old plant in a shaded trial garden in Zeeland, Michigan with supplemental water and fertilizer.

Botanical classification: *Hosta* x hybrid;

Parentage: Female or seed parent is WGI-22A; male or pollen parent is 'Empress Wu';

Propagation: Garden division and sterile shoot tip tissue culture;

Time to initiate roots from tissue culture: About two to three weeks;

Growth rate: Moderately vigorous;

Crop time: About three months to four months to finish during the spring in a one-liter container from rooted tissue culture plantlet during the warm portion of the growing season;

Rooting habit: Fleshy, lightly branching;

Root color: Nearest RHS NN155C when actively growing;

Plant shape and habit: Hardy herbaceous perennial with basal rosette of leaves emerging from rhizomes producing a low medium-sized mound of outwardly extending petioles and leaves and arching scapes flowering above foliage;

Plant size: Foliage height to about 89 cm above soil line to the top of the leaves, to about 72 cm tall to the top of the flowers and to about 226 cm wide at the widest point just above the soil line;

Foliage description: Broadly ovate; narrowly acute to apiculate apex; cordate base with lobes frequently overlapping; margin entire; flat and not bullate between the veins, veins deeply impressed; glabrous and smooth both surfaces; lustrous adaxial; slightly glaucous abaxial; flexible; variegated;

Leaf blade size: To about 38.1 cm long and about 30.5 cm wide about one-third way from the base;

Leaf blade color: Early season and expanding adaxial margin between RHS 144A and RHS 144B, center between RHS 146B and RHS 147B, with intermediate zone comprising nearest RHS 137C and between RHS 146B and RHS 146C; abaxial early season and expanding margin between RHS 147C and RHS 146D, center between RHS 191B and RHS 137C, with intermediate zone comprising RHS 144A, RHS 146D, and between RHS 191B, RHS 148B and RHS 148C; mid-season and mature adaxial margin between RHS 8D and RHS 11D, center nearest RHS NN137B, with intermediate zone comprising colors of between RHS 193B and RHS 193C, between RHS 150D and RHS 147D, nearest RHS 137B, and nearest RHS 193A; abaxial mid-season and mature margin nearest RHS 11D, center between RHS N138B and RHS N138C, with intermediate zone comprising colors of between RHS 148B and RHS 148C, between RHS N144D and RHS 147D, and nearest RHS N144D;

Veins: 14 to 16 pairs with midrib; impressed adaxial and costate and smooth abaxial;

Vein color: Young adaxial margin region nearest RHS 148D and center nearest RHS 146B, young abaxial margin region nearest RHS 146D and center nearest RHS 138B; mature adaxial margin nearest RHS 150D, and center nearest RHS 146D, mature abaxial margin nearest RHS 148D and center between RHS 139D and RHS 148C;

Petiole: Glabrous, slightly glaucous, and matte both adaxial and abaxial; concavo-convex; stiff; to 42 cm long and 20 mm wide at base and about 8 mm deep; with a lightly variegated margin about 1 to 2 mm wide;

Petiole color: Adaxial and abaxial margin between RHS 4B and RHS 4A, center between RHS 146D and RHS 145A;

Flower description:

Buds one to two days prior to opening: Clavate with acute apex and narrow tube and rounded base; about 48 mm long and 12 mm in diameter at the widest portion in the bulb, tube to about 15 mm long and to about 3 mm diameter near base, gradually tapering from bulb;

Bud color: Distal two-thirds of bulb nearest RHS NN155C with faint blush of nearest RHS 76B, proximal one-third of bulb and distal corolla tube nearest RHS NN155C, proximal corolla tube nearest RHS 157D;

Inflorescence: Flowering portion about 15 cm long and 9 cm wide; with hyaline bracts subtending each flower;

Flower bracts: Typically, one subtending each flower; lanceolate; scarious; narrowly acute apex; truncate and clasping base; entire margin; glabrous and matte abaxial and adaxial; drying just after flower opens; to about 23 mm long and 8 mm wide at base, decreasing distally;

Flower bract color: Adaxial and abaxial proximally nearest RHS NN155B with a faint blush of nearest RHS 76D, distally between RHS 145D and RHS 144D both adaxial and abaxial;

Flowers: Perfect; incomplete; broadly campanulate; attitude outwardly to slightly downwardly; to about 60 mm long to exserted pistil; corolla to 55 mm long and 47 mm wide at apex, fused in basal 31 mm, free in the distal 25 mm, decreasing in size distally; corolla tube portion 31 mm long, 13 mm wide at fusion, and gradually tapering to 3 mm diameter in middle; with rounded base; flowers tightly arranged on scape;

Flowering lasting: Persists for a normal period, usually about one day on plant;

Flowering period: Scapes remain effective with flowers beginning early July for about three weeks; with about 30 flowers per scape; mostly secund;

Fragrance: No detectable fragrance;

Tepal: Two sets of three; lanceolate; entire margins; acute apex; fused in basal 31 mm and free in the distal 24 mm; glabrous adaxial and abaxial; outer set to about 9 mm wide and 55 mm long; inner set to about 10 mm wide and 55 mm long;

Tepal color: Outer and inner sets identical; adaxial between RHS 76D and RHS NN155D in the longitudinal center and nearest RHS NN155D along the margins and the corolla tube, abaxial nearest RHS NN155D in the blade and the corolla tube;

Gynoecium: Single; to about 61 mm long; superior;

*Style*.—Cylindrical; glabrous; to about 53 mm long and 0.5 mm diameter; proximally straight with distal 8 mm arcuate upwards 90°; color nearest RHS NN155B distally and proximally nearest RHS 155C.

*Stigma*.—Globose; puberulent; about 1 mm long and 1 mm diameter; color nearest RHS NN155A.

*Ovary*.—Ellipsoidal; superior; apex acute; base rounded to truncate; sides deeply furrowed; about 7 mm long and 2.5 mm diameter; color between RHS 145A and RHS 144B.

Androecium: Six;

*Filaments*.—Six; cylindrical; approximately 51 mm long and 0.5 mm in diameter; arcuate upwardly about 180° in the distal 11 mm; color nearest RHS NN155B distally and proximally nearest RHS 155C.

*Anthers*.—Oblong; with rounded ends; dorsifixed; longitudinal; about 4.5 mm long and 2 mm wide when fully developed in unopened flower; color between RHS 197B and RHS 199B.

*Pollen*.—Abundant; spherical; less than 0.1 mm long; color nearest RHS 10B.

Peduncle: Cylindrical; nearly one per mature division; about 6 per plant; glabrous; moderately glaucous; aspect arching to outwardly; to about 56 cm long, and about 6 mm in diameter at base, average about 53 cm long and 5.5 mm diameter at base;

Peduncle color: Between RHS 138B and RHS 148C;

Pedicel: Cylindrical; glabrous; slightly lustrous; to about 10 mm long and 2 mm diameter; slightly arcuate; attitude outwardly to slight downwardly;

Pedicel color: Proximally between RHS 143A and RHS 143B, distally nearest RHS 76D;

Scape bracts: Typically three below first flower; lanceolate; narrowly acute apex and truncate base and clasping; entire margin; glabrous and slightly glaucous abaxial and adaxial; to about 48 mm long 11 mm across at base, decreasing distally;

Scape bract color: Adaxial and abaxial proximally nearest RHS NN155B with a faint blush of nearest RHS 76D, distally between RHS 145D and RHS 144D both adaxial and abaxial;

Fruit: Not observed under the present growing conditions;

Seeds: Not yet observed;

Disease resistance: Resistance and susceptibility to pests (including: *Odocoileus virginianus* and *Oryctotagus cuniculus*) and diseases common to *Hostas* is equal that typical of other cultivars.

Growth: The plant grows best and shows best coloration with plenty of moisture, adequate drainage and light shade, but is able to tolerate some drought when mature.

Hardiness: At least from USDA zone 3 through 8, and other disease resistance is typical of that of other *Hostas*.

It is claimed:

1. A new and distinct *Hosta* plant named 'Brontosaurus' as herein described and illustrated.

* * * * *